(12) United States Patent
van der Plaats et al.

(10) Patent No.: US 9,756,848 B2
(45) Date of Patent: Sep. 12, 2017

(54) APPARATUS, SYSTEM AND METHOD FOR CONDITIONING AND PRESERVING AN ORGAN FROM A DONOR

(75) Inventors: Arjan van der Plaats, Winschoten (NL); Gerhard Rakhorst, Groningen (NL)

(73) Assignee: ORGAN ASSIST B.V., Groningen (NL)

( * ) Notice: Subject to any disclaimer, the term of this patent is extended or adjusted under 35 U.S.C. 154(b) by 0 days.

(21) Appl. No.: 14/342,149

(22) PCT Filed: Sep. 2, 2011

(86) PCT No.: PCT/NL2011/050603
§ 371 (c)(1),
(2), (4) Date: Apr. 14, 2014

(87) PCT Pub. No.: WO2013/032319
PCT Pub. Date: Mar. 7, 2013

(65) Prior Publication Data
US 2014/0220550 A1    Aug. 7, 2014

(51) Int. Cl.
*A01N 1/02* (2006.01)

(52) U.S. Cl.
CPC ................ *A01N 1/0247* (2013.01)

(58) Field of Classification Search
None
See application file for complete search history.

(56) References Cited

U.S. PATENT DOCUMENTS

| | | | |
|---|---|---|---|
| 3,753,865 A * | 8/1973 | Belzer et al. | 435/284.1 |
| 5,141,847 A | 8/1992 | Sugimachi et al. | |
| 5,285,657 A | 2/1994 | Bacchi et al. | |
| 5,338,662 A | 8/1994 | Sadri | |
| 5,356,771 A | 10/1994 | O'Dell | |
| 5,385,821 A | 1/1995 | O'Dell et al. | |
| 5,476,763 A | 12/1995 | Bacchi et al. | |
| 5,514,536 A | 5/1996 | Taylor | |
| 5,586,438 A | 12/1996 | Fahy | |
| 5,716,378 A | 2/1998 | Minten | |
| 5,827,222 A | 10/1998 | Klatz et al. | |
| 5,856,081 A | 1/1999 | Fahy | |
| 6,100,082 A | 8/2000 | Hassanein | |
| 6,555,057 B1 | 4/2003 | Barbut et al. | |
| 6,642,045 B1 * | 11/2003 | Brasile | 435/284.1 |
| 6,677,150 B2 | 1/2004 | Alford et al. | |
| 6,803,227 B2 | 10/2004 | Wood et al. | |
| 6,811,965 B2 | 11/2004 | Vodovotz et al. | |
| 6,905,871 B1 | 6/2005 | Doorschodt et al. | |
| 6,946,099 B2 | 9/2005 | Vijay et al. | |
| 6,953,655 B1 | 10/2005 | Hassanein et al. | |
| 7,176,015 B2 | 2/2007 | Alford et al. | |
| 7,651,835 B2 | 1/2010 | Hassanein et al. | |
| 7,678,563 B2 | 3/2010 | Wright et al. | |
| 7,691,622 B2 | 4/2010 | Garland et al. | |
| 7,811,808 B2 | 10/2010 | Van Der Plaats et al. | |
| 7,998,725 B2 | 8/2011 | Schein et al. | |
| 8,097,449 B2 | 1/2012 | Garland et al. | |
| 8,211,628 B2 | 7/2012 | Thatte et al. | |
| 8,287,580 B2 | 10/2012 | Rakhorst et al. | |
| 8,389,271 B2 | 3/2013 | Wright et al. | |
| 2003/0054540 A1 | 3/2003 | Alford et al. | |
| 2003/0108530 A1 | 6/2003 | Brodt et al. | |
| 2004/0082057 A1 | 4/2004 | Alford et al. | |
| 2004/0224299 A1 | 11/2004 | Garland et al. | |
| 2004/0235142 A1 | 11/2004 | Schein et al. | |
| 2004/0248281 A1 | 12/2004 | Wright et al. | |
| 2005/0147958 A1 | 7/2005 | Hassanein et al. | |
| 2005/0153271 A1 | 7/2005 | Wenrich | |
| 2007/0009881 A1 | 1/2007 | Arzt et al. | |
| 2007/0026376 A1 | 2/2007 | Lee et al. | |
| 2007/0184545 A1 | 8/2007 | Plaats et al. | |
| 2008/0038811 A1 | 2/2008 | Alford et al. | |
| 2008/0096184 A1 * | 4/2008 | Brasile | 435/1.2 |
| 2009/0020412 A1 | 1/2009 | Takenouchi et al. | |

(Continued)

FOREIGN PATENT DOCUMENTS

| | | |
|---|---|---|
| EP | 0479635 A1 | 4/1992 |
| EP | 1168913 | 1/2002 |

(Continued)

OTHER PUBLICATIONS

St. Peter, Shawn D; et al; "Liver and kidney preservation by perfusion" The Lancet, 359, 604-613, 2002.*
Bjorken, C; et al ; "A technique for rapid harvesting of cadaveric renal and pancreatic grafts after circulatory arrest" British Journal of Surgery, 63, 517-519, 1976).*
Brasile, L. et al; "Postmortem Organ Salvage Using Oxygent Supplemented Perfusate" Artificial Cells, Blood Substitutes and Biotechnology, 22, 1469-1475, 1994.*
Gonzalez, F.X., et al., "Adenine Nucleotide Liver Tissue Concentrations From Non-Heart-Beating Donor Pigs and Organ Viability After Liver Transplantation", Transplantation Proceedings, vol. 29, 1997, pp. 3480-3481.

(Continued)

*Primary Examiner* — David Berke-Schlessel
(74) *Attorney, Agent, or Firm* — Pearne & Gordon LLP

(57) ABSTRACT

A donor organ treatment apparatus has a container for holding an organ and a perfusion liquid circuit. The perfusion circuit includes a supply conduit downstream of an oxygenator and a heat exchanger for supplying perfusion liquid from the oxygenator and the heat exchanger to an organ in the container and a return conduit upstream of the oxygenator and the heat exchanger for guiding perfusion liquid from the organ inside the container to the oxygenator and the heat exchanger. The supply conduit is provided with an outlet port coupling for connection to a perfusion catheter and the return conduit is provided with an inlet port coupling for connection to a return catheter. A method for successively perfusing an organ in-situ and ex-vivo with liquid circulating through the same perfusion circuit is also described.

6 Claims, 10 Drawing Sheets

(56) References Cited

U.S. PATENT DOCUMENTS

| | | |
|---|---|---|
| 2009/0291486 A1 | 11/2009 | Wenrich |
| 2010/0112542 A1 | 5/2010 | Wright et al. |
| 2010/0151435 A1 | 6/2010 | Thatte et al. |
| 2010/0151559 A1 | 6/2010 | Garland et al. |
| 2010/0234928 A1 | 9/2010 | Rakhorst et al. |
| 2011/0033916 A1 | 2/2011 | Hutzenlaub et al. |
| 2011/0065170 A1 | 3/2011 | Fondevila Campo et al. |
| 2012/0264103 A1 | 10/2012 | Thatte et al. |
| 2012/0282591 A1 | 11/2012 | Thatte et al. |

FOREIGN PATENT DOCUMENTS

| | | |
|---|---|---|
| EP | 1677593 | 7/2006 |
| EP | 2124539 A2 | 12/2009 |
| WO | 0170950 | 9/2001 |
| WO | 02089571 A1 | 11/2002 |
| WO | 03024214 | 3/2003 |
| WO | 2004089235 A2 | 10/2004 |
| WO | 2005009125 A1 | 2/2005 |
| WO | 2006118990 | 11/2006 |
| WO | 2007111495 A1 | 10/2007 |
| WO | 2009041806 A1 | 4/2009 |
| WO | 2009138446 A2 | 11/2009 |

OTHER PUBLICATIONS

Arias-Diaz, J., et al., "Changes in Adenine Nucleotides and Lipid Hydroperoxides During Normothermic Cardiopulmonary Bypass in a Porcine Model of Type II Non-Heart-Beating Donor", Transplantation Proceedings, vol. 29, 1997, pp. 3486-3487.

Garcia-Valdecasas, J.C., et al., "Evaluation of Ischemic Injury during Liver Procurement from Non-Heart-Beating Donors", Eur Surg Res, vol. 31, 1999, pp. 447-456.

Tabet, J., et al., "Evaluation to Ischemic Liver Injury During Graft Procurement From Non-Heart-Beating Donor Pigs", Transplantation Proceedings, vol. 29, 1997, pp. 3482-3483.

Schon, Michael R., et al., "The Possibility of Resuscitating Livers After Warm Ischemic Injury", Transplantation, vol. 56, No. 1, Jul. 1993, pp. 24-31.

* cited by examiner

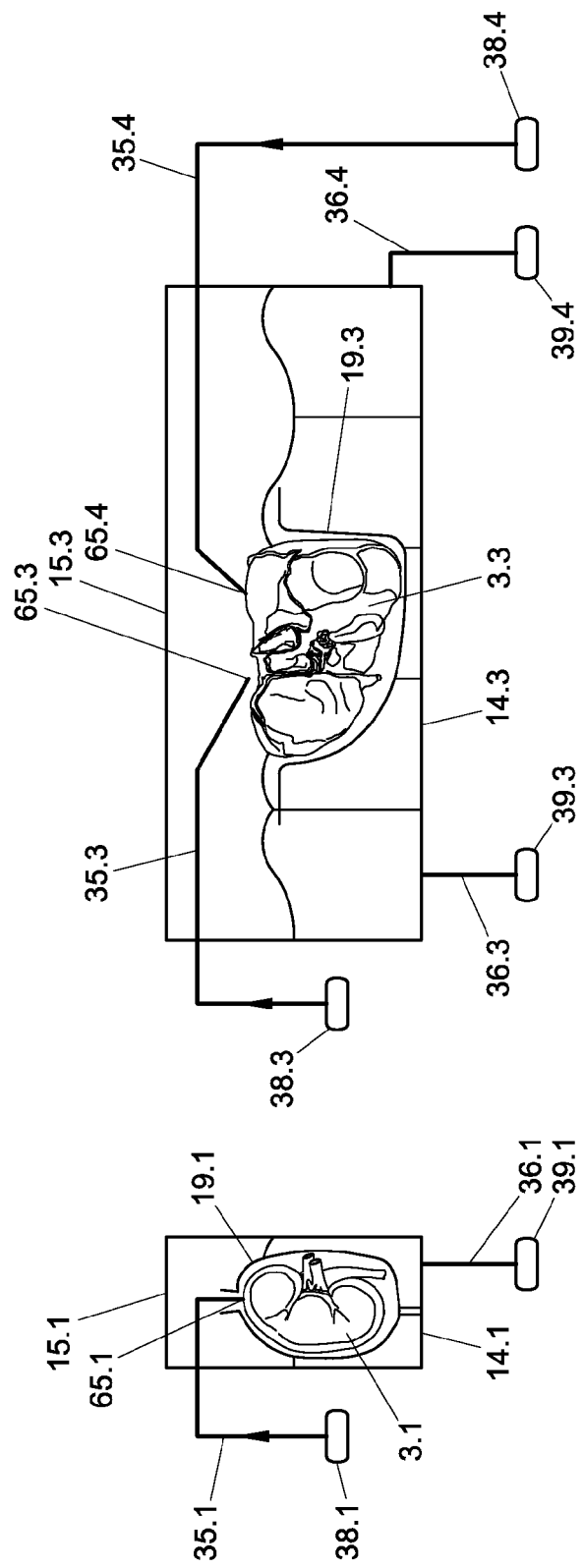

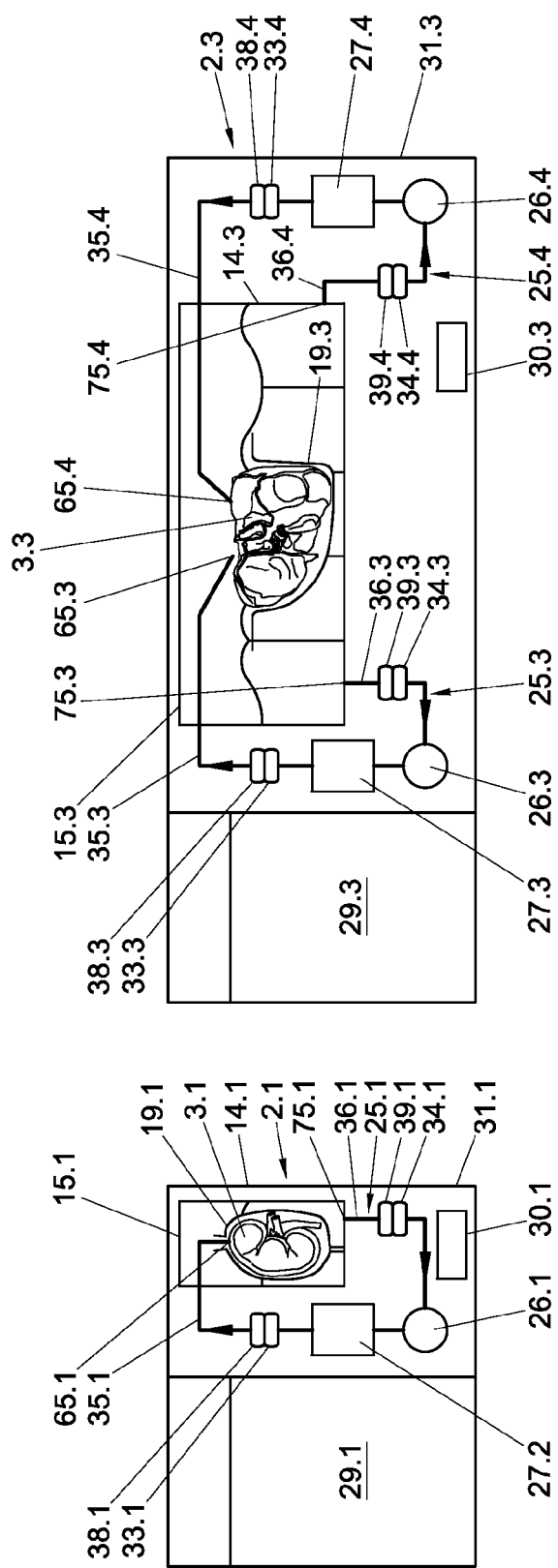

APPARATUS, SYSTEM AND METHOD FOR CONDITIONING AND PRESERVING AN ORGAN FROM A DONOR

FIELD AND BACKGROUND OF THE INVENTION

The invention relates to an apparatus, a system and a method for conditioning and preserving an organ from a donor.

Transplantation of an organ from a donor to a patient involves three stages, 1) the donor operation, 2) the preservation and transportation of the organ and 3) the implantation in the patient.

In most cases the donor is a deceased human, but some donor organs (for instance one of the kidneys) or parts thereof are sometimes donated by living humans.

In the common preservation procedure, known as "static cold storage" (CS), after the initial wash out with preservation liquid, the organ is packed sterile in a bag filled with preservation liquid, which in turn is placed in a bag with cold saline to prevent direct contact with ice in the box in which the packed organ is stored for transport. This bag is in turn placed in a third bag for sturdiness and to avoid a disturbance of sterile conditions and is finally stored in the cooling box with the melting ice.

A drawback of this procedure is the possibility of organ decay due to e.g. a lack of perfusion that enables the delivery of oxygen and the removal of waste products, an unusual position of the organ, or tissue injury due to (too) direct heat exchange with ice.

In international patent application WO2005/009125, a portable preservation apparatus is described that allows continuous perfusion of an organ and includes a pulsating pump system integrated in a cooling box with a cold oxygenated preservation liquid (4° C.). Besides delivery of oxygen to the organ, the cold oxygenated preservation liquid also provides for cooling of the organ, administration of nutritients and removal of waste products. An organ chamber intended to cooperate with such a device has to meet extra demands concerning structure and connections, while still complying with requirements of sterile handling and ease-of-use. The organ is transported in a bag filled with preservation liquid in which the organ has been placed immediately after explantation from the deceased donor and canulas are connected to the organ.

In international patent application WO2004/089235, an apparatus for transport and storage of an organ is described, which includes a cassette for carrying the organ and a volume of the perfusion liquid. The cassette is provided with tubing for connection to an organ and/or to remove medical liquid from the organ container, and a connection device(s) for connecting the tubing to tubing of a perfusion apparatus, a transporter or a diagnostic device.

SUMMARY OF THE INVENTION

It is an object of the present invention to improve the conditioning of organs from deceased donors for implantation into patients.

According to the invention, this object is achieved by providing an apparatus according to claim 1. The invention can also be embodied in a system according to claim 9 which includes such an apparatus and in a method according to claim 15 for which the apparatus according to the invention is specifically adapted.

The invention allows carrying out both in-situ perfusion and perfusion of the explanted organ (i.e. ex-vivo) via, at least for a substantial part, the same perfusion circuit. Particular advantages of perfusing via the same perfusion circuit are that the composition and temperature of the perfusion liquid is ensured to be virtually the same during in-situ perfusion and subsequent ex-vivo perfusion of the explanted organ and that the need of bringing a second perfusion circuit in a condition ready for use and adapted to the operating parameters of the first perfusion circuit is avoided. Thus, it is avoided that the organ is subjected to a sudden change in temperature and composition of the perfusion liquid and also mistakes in this respect and a potential source of contamination are avoided.

Particular elaborations and embodiments of the invention are set forth in the dependent claims.

Further features, effects and details of the invention appear from the detailed description and the drawings.

BRIEF DESCRIPTION OF THE DRAWINGS

FIGS. 6 and 7 are schematic representations of examples of organ containers of an apparatus according to the invention, separated from the associated treatment unit;

FIGS. 8 and 9 are schematic representations of examples of a transport unit of system according to the invention.

DETAILED DESCRIPTION

Figure 1:
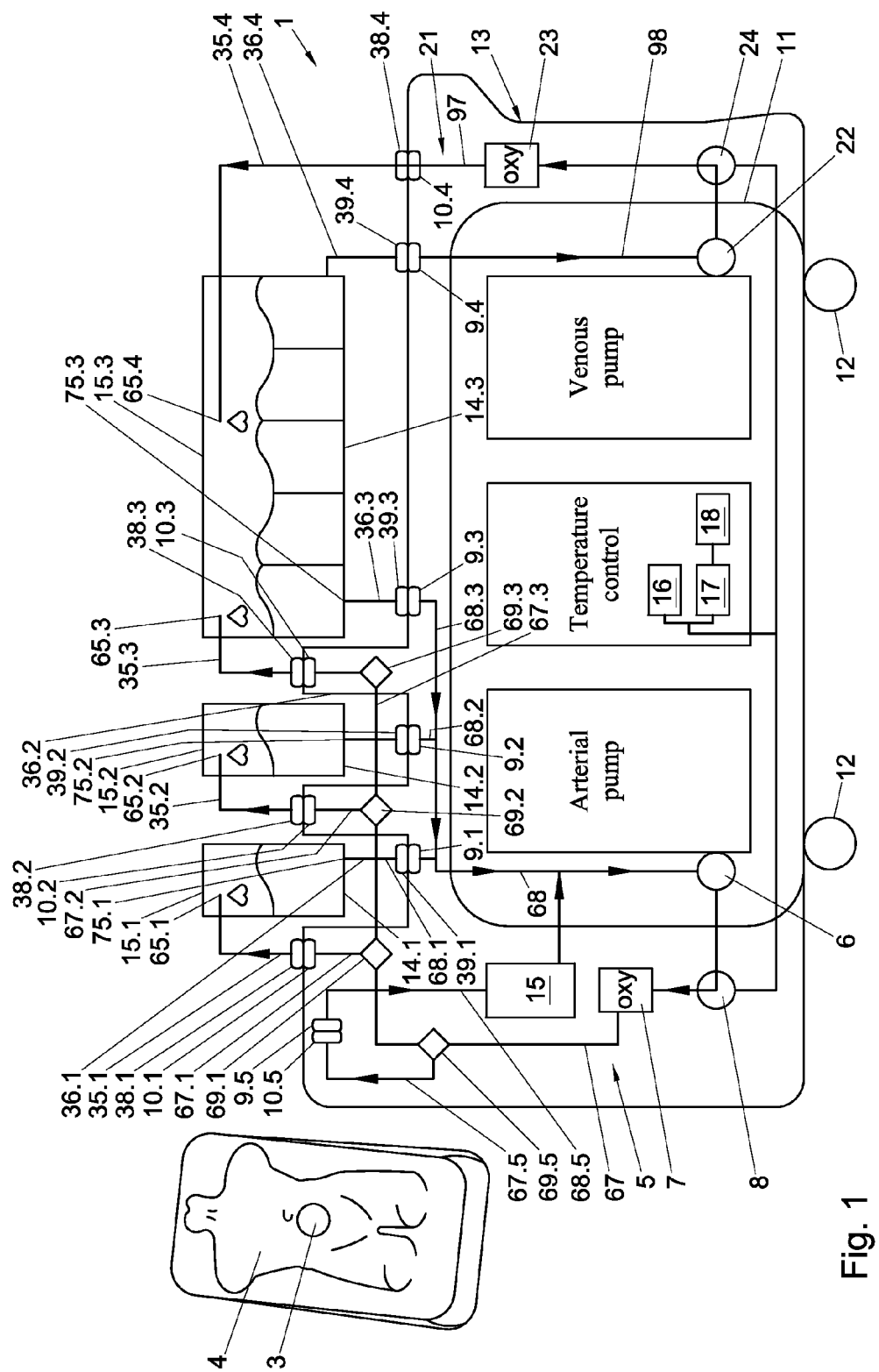
FIGS. 1-5, 10 and 11 are schematic representations of an example of a treatment apparatus according to the invention in various configurations and stages of operation.

First an example of an organ treatment apparatus 1 shown in FIGS. 1-5, 10 and 11 and examples of organ transport units 2.1, 2.3 are shown in FIGS. 8 and 9 are described. Together, the treatment apparatus 1 and the transport unit 2 constitute a system for preserving organs 3 of a deceased donor 4 for implantation into a patient.

The organ treatment apparatus 1 includes a first perfusion liquid circuit 5 equipped with a pulsatile pump 6, an oxygenator 7 and a heat exchanger 8 for cooling or warming liquid in the perfusion liquid circuit 5 passing through the heat exchanger 8. The perfusion liquid circuit 5 extends between supply ends 65.1, 65.2, 65.3 and return inlet ends 75.1, 75.2, 75.3 in organ containers 14.1, 14.2 and 14.3. A second perfusion liquid circuit 21 is provided for providing venous perfusion of a liver 3.3. The second perfusion liquid flow circuit 21 is equipped with a second, non-pulsatile pump 22, a second oxygenator 23 and a second heat exchanger 24 communicating with the temperature control for at least cooling or heating liquid in the second perfusion liquid circuit 5 passing the heat exchanger 24. The second perfusion liquid circuit 21 further includes a second supply conduit 97 downstream of the second oxygenator 23 and the second heat exchanger 24 for supplying perfusion liquid from the second oxygenator 23 and the second heat exchanger 24 to the liver 3.3 in the liver container 14.3, and a second return conduit 98 upstream of the second oxygenator 23 and the second heat exchanger 8 for guiding perfusion liquid from the liver 3.3 in the liver container 14.3 to the second oxygenator 23 and the second heat exchanger 24. The non-pulsatile flow generated by the second pump 22 is advantageous for an effective perfusion of the venous flow structure of the liver.

For a modular configuration it is advantageous if the two pumps are mutually identical, but can be set to operate in a pulsatile mode or a non-pulsatile operating mode, depending on the required perfusion flow characteristics.

A frame of the apparatus 11 is carried by wheels 12 for easy displacement through a hospital. The organ containers 14.1, 14.2 and 14.3 are each equipped with a sterile cover 15.1, 15.2, 15.3 which is removable for allowing an organ to be placed in the container 14.1, 14.2 and 14.3 and to be removed from the container 14.1, 14.2 and 14.3.

The perfusion liquid circuit 5 further has a supply conduit 67 with branches 67.1, 67.2, 67.3 downstream of the oxygenator 7 and the heat exchanger 8 for supplying perfusion liquid from the oxygenator 7 and the heat exchanger 8 to organs 3.1, 3.2, 3.3 in the containers 14.1, 14.2, 14.3. Furthermore, the perfusion liquid circuit 5 has a return conduit 68 with branches 68 68.1, 68.2, 68.3 upstream of the oxygenator 7 and the heat exchanger 8 for guiding perfusion liquid from the organs 3.1, 3.2, 3.3 in the containers 14.1, 14.2, 14.3 to the oxygenator 7 and the heat exchanger 8.

Figure 2:
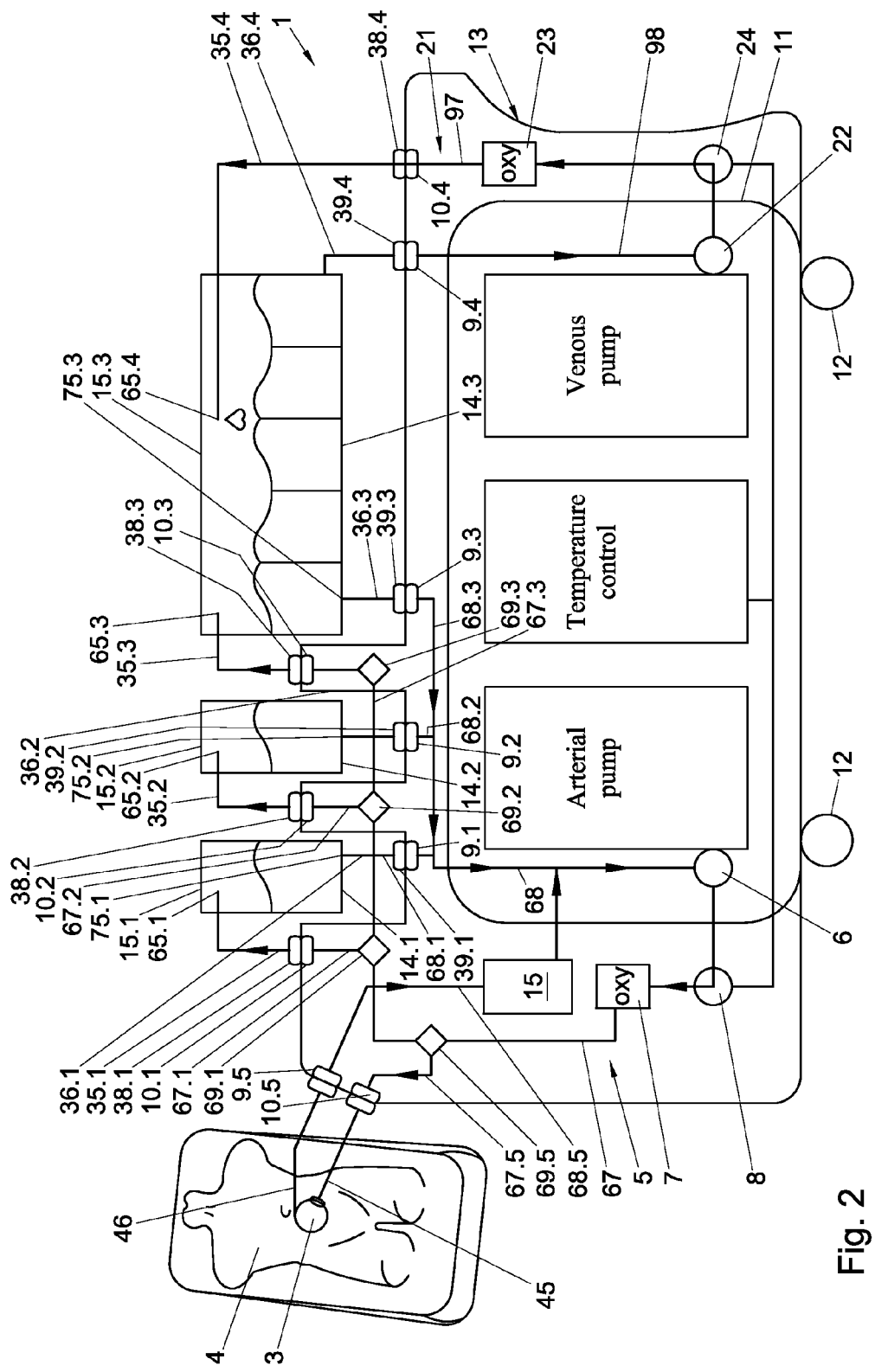
Figure 3:
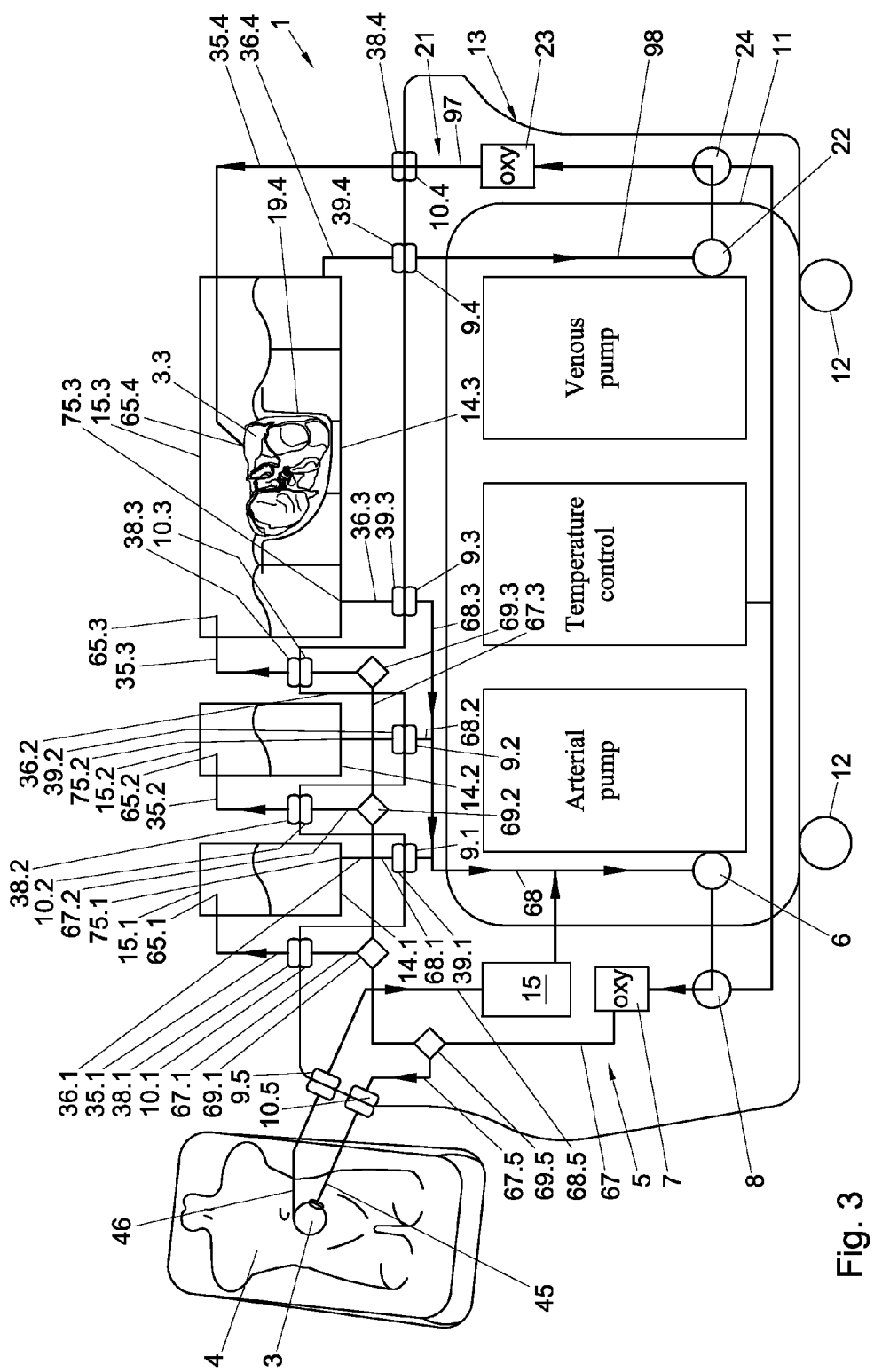
Figure 4:
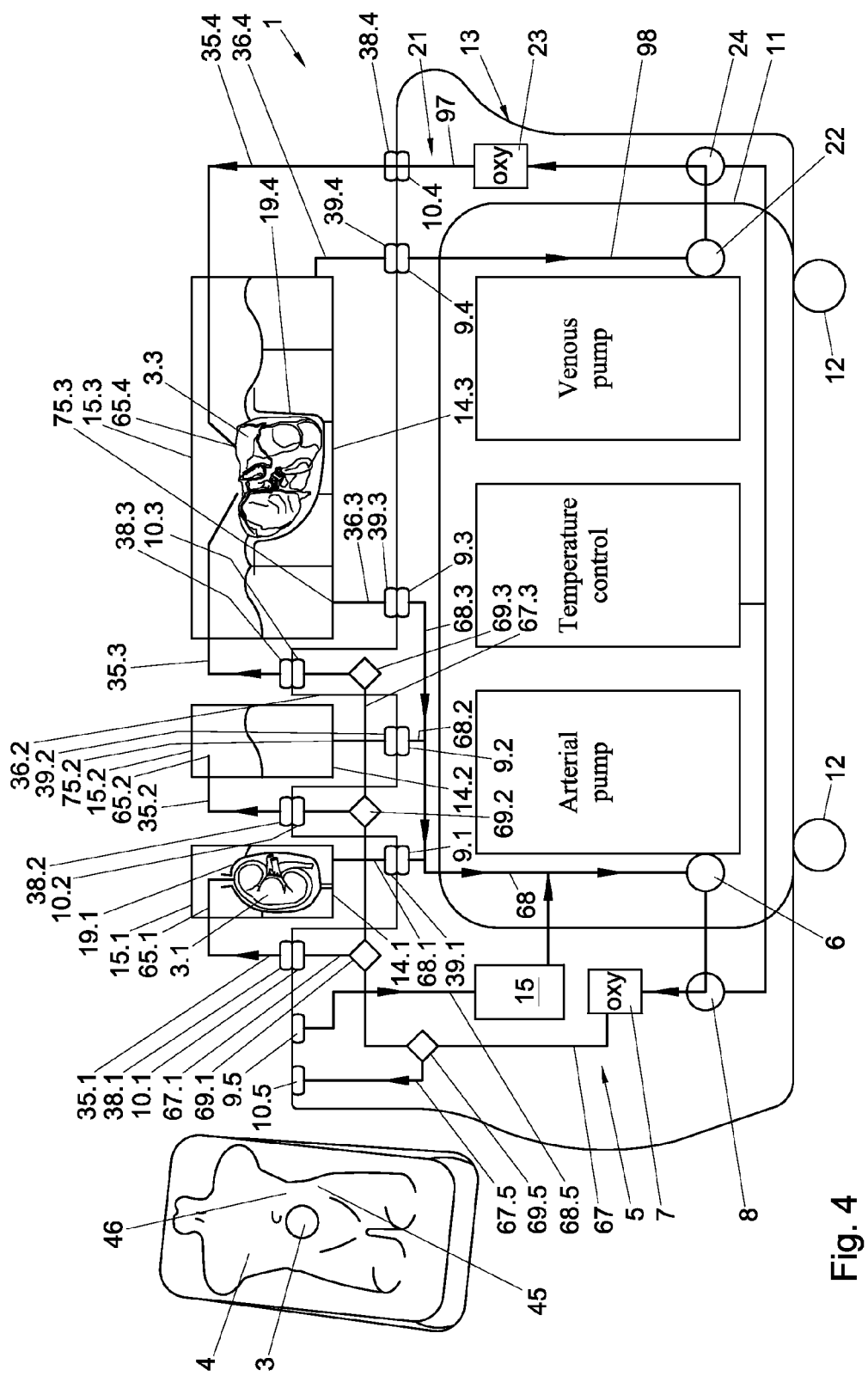

The supply conduit 67 further has a branch 67.5 provided with an outlet port coupling 10.5 for connection to a perfusion catheter 45 (FIGS. 2 and 3). The return conduit 68 further has a branch 68.5 provided with an inlet port coupling 9.5 for connection to a return catheter 46 (FIGS. 2 and 3) and a perfusion liquid buffer reservoir 15. The perfusion liquid reservoir 15 provides an increase of the volume of liquid in the perfusion circuit. This is of particular relevance during perfusion of the organs before explantation from the donor, because in that situation there is no volume of perfusion liquid in an organ container or the like. In a small volume of circulating perfusion liquid concentrations of metabolic products can more easily rise to toxic levels than in a larger volume of circulating perfusion liquid.

Valves 69.1, 69.2, 69.3, 69.5 are provided for allowing and blocking perfusion liquid flow to the branches 67.1, 67.2, 67.3 of the perfusion liquid circuit 5.

The heat exchanger 8 is connected in heat exchanging relationship with a heater 16 and with a cooler 17. The heater and the cooler may also be integrated, for instance in a reversible-cycle heat pump. The cooler is connected in heat exchanging relationship with a further heat exchanger 18 for dissipating heat resulting from cooling liquid in the heat exchanger 8. (The heater 16, the cooler 17 and the further heat exchanger 18 are shown in FIG. 1 only.) The heat exchangers 8, 18, the heater 16 and the cooler 17 have sufficient capacity to cool organs 3.1, 3.2, 3.3 in the containers 14.1, 14.2 and 14.3 to a temperature of 4° C. More in general, the cooling capacity when operating at room temperature (18-22° C.) as the ambient temperature is preferably sufficient cool the organ(s) to less than 8° C. and preferably to a temperature of less than 4° C., preferably at a rate of at least 1° C./minute and to keep the organs at that temperature as well as for rewarming the organs 3.1, 3.2, 3.3 back or nearer to 37° C. (body temperature) and keeping the organs 3.1, 3.2, 3.3 in pre-warmed condition prior to implantation.

In the present example, the organs 3.1 and 3.2 are kidneys and the organ 3.3 is a liver. However, suitably adapted containers may be used for conditioning and preserving other perfusable organs (the term "organ" also being understood as encompassing a part of an organ and a body part composed of different types of organ tissue) such as a heart, a pair of lungs, a single lung, a pancreas or a limb. The containers 14.1, 14.2 and 14.3 may each be equipped with a support cartridge 19.1, 19.2, 19.3 for resiliently supporting the organs 3.1, 3.2, 3.3 in the containers 14.1, 14.2 and 14.3, for instance as is disclosed in applicant's international patent application WO2009/041806. Preferably, the supply ends 65.1, 65.2, 65.3 of the perfusion liquid circuit 5 are equipped with fittings for connection to blood vessels of or connected to the organ.

The portable transport units 2.1, 2.3 (FIGS. 8 and 9) are separate from the organ treatment apparatus 1 and self-sufficient for a period of time that is long enough to control the temperature and perfusion of an organ therein during transportation from an explantation site to an implantation site. For this purpose, the transport units 2.1, 2.3 are preferably self-sufficient for at least 24 hours.

Also, the transport units 2.1, 2.3 each have a perfusion liquid circuit 25.1, 25.3, equipped with a pump 26.1, 26.3 and an oxygenator 27.1, 27.3. The transport unit 2.3 shown in FIG. 9 is a liver transport unit, which has a second perfusion liquid circuit 25.4 with a second pump 26.4 and a second oxygenator 27.5 for venous perfusion of a liver 3.3 in the container 14.3 in the transport unit 2.3. An energy storage in the form of a battery is connected to a drive 29.1, 29.3 of the pump 26.1, 26.3 for providing energy to the pump drive 29.1, 29.3 for driving the pump 26.1, 26.3.

The transport units 2.1, 2.3 each have an outer wall 31 and cover 32 of thermally insulating material to limit heat exchange with the environment, so that a unit 30.1, 30.3 with thermal capacity, such as an ice pack, or ice adjacent the organ is sufficient for maintaining the temperature of the organ 3.1, 3.3 in the transport unit 2.1, 2.3 below a required maximum during transportation of the organ, without supply of energy for a cooler from the outside. However, a cooler or a reversible cycle heat pump that may optionally be connectable to a power supply, e.g. 12V DC in a motor vehicle, may also be provided. The battery is mounted generally at the outside of the insulating material, to keep the battery away from the low temperature inside the transport unit and to avoid heat emission from the battery inside the transport unit 2.1, 2.3.

The perfusion liquid circuits 25.1, 25.3, 25.4 between the supply ends 65.1, 65.3, 65.4 and the return inlet ends 75.1, 75.3, 75.4 in the organ containers 14.1 and 14.3.

As can be seen in FIG. 1, the supply outlet ends 65.1, 65.2, 65.3, 65.4 of the perfusion liquid circuits in the containers 14.1, 14.2, 14.3 are provided at the ends of container sections 35.1, 35.2, 35.3, 35.4 of the supply conduits 67.1, 67.2, 67.3, 97 for connection to a blood vessel of an organ 3.1, 3.2, 3.3 in the container 14.1, 14.2, 14.3. The return inlet ends 75.1, 75.3, 75.4 of the perfusion liquid circuits in the containers 14.1, 14.2, 14.3 are provided at the ends of container sections 36.1, 36.2, 36.3, 36.4 of the return conduits 68.1, 68.2, 68.3, 98. The container sections 35.1, 35.2, 35.3, 35.4 of the supply conduits 67.1, 67.2, 67.3, 97 extend from inlet port couplings 38.1, 38.2, 38.3, 38.4 of the containers 14.1, 14.2, 14.3. The container sections 36.1, 36.2, 36.3, 36.4 of the return conduits 68.1, 68.2, 68.3, 98 extend from inlet port couplings 39.1, 39.2, 39.3, 39.4 of the containers 14.1, 14.2, 14.3.

In FIG. 1, the inlet and outlet port couplings 38.1, 38.2, 38.3, 38.4, 39.1, 39.2, 39.3, 39.4 of the containers 14.1, 14.2, 14.3 are coupled to inlet and outlet port couplings 9.1, 9.2, 9.3, 9.4, 10.1, 10.2, 10.3, 10.4 of a treatment unit portion 13 of the apparatus 1. By disconnecting these couplings, the containers 14.1, 14.2, 14.3 can be disconnected from the treatment unit portion 13 of the apparatus 1 so that the inlet and outlet port couplings 38.1, 38.2, 38.3, 38.4, 39.1, 39.2, 39.3, 39.4 of the containers 14.1, 14.2, 14.3 can be releasably connected to corresponding sets of the couplings 33.1, 33.3, 33.4, 34.1, 34.3, 34.4 of a suitable one of the inlet and outlet port couplings of the transport units 2.1, 2.3 (FIGS. 8 and 9). The transport unit inlet and outlet port couplings 33.1, 33.3, 33.4, 34.1, 34.3, 34.4 and the inlet and outlet port couplings 38.1, 38.2, 38.3, 38.4, 39.1, 39.2, 39.3, 39.4 of the containers as well as the inlet and outlet port couplings 9.1, 9.2, 9.3, 9.4, 10.1, 10.2, 10.3, 10.4 of the treatment unit portion 13 of the apparatus 1 may be arranged in such configurations that the container inlet and outlet port couplings 38.1, 38.2, 38.3, 38.4, 39.1, 39.2, 39.3, 39.4 of at least one of the containers and preferably of each of the containers 14.1, 14.2 can be simultaneously plugged into the outlet and inlet port couplings 33.1, 33.3, 33.4, 34.1, 34.3, 34.4 of one of the transport units 2.1, 2.2 or into a corresponding set of the outlet and inlet port couplings 9.1, 9.2, 9.3, 9.4, 10.1, 10.2, 10.3, 10.4 of the treatment unit portion 13 of the apparatus 1.

In use, the perfusion liquid circuit 5 is first filled with a priming solution which is then circulated for de-airing of the circuit, oxygenation of the solution and bringing the solution to a desired starting temperature, in a configuration shown in FIG. 1. In that configuration inlet and outlet port couplings 9.5, 10.5 for coupling to perfusion and return catheters are connected to each other, so that also the branches 67.5 and 68.5 of the supply and return conduits 67, 68 are included in the preparation of the system.

Next, the inlet and outlet port couplings 9.5, 10.5 for coupling to perfusion and return catheters are disconnected from each other and, if the donor is a deceased person, coupled to perfusion and return catheters 45, 46, which are or have been inserted into the deceased donor 4 as is shown in FIG. 2. The valves 69.1, 69.2, 69.3, 69.5 are set for leading perfusion liquid flow into the branch 67.5 and accordingly into the catheter 45. The pump 6 and temperature control 8 are then activated and the organs 3 in the deceased donor 4 are perfused. This may involve flushing with disposal of return fluid and subsequently perfusion in a circulating fashion as is described in applicant's international patent application WO 2007/111495.

After perfusion via the donor's vascular system or, if the organ is from a live donor, as the first organ perfusion, the organ may also be continue to be perfused prior to (completion of the explantation from the donor body via conduits coupled to arterial and venous ends dissected from the vascular system of the donor body and in communication with the organ. For that purpose, the inlet and outlet port couplings 9.5, 10.5 may be connected to tubing constituting the conduits coupled or to be coupled to the severed arterial and venous ends of the organ to be perfused.

The perfusion of the organ is then stopped and the organ is taken out of the donor body. If the organ is perfused via the severed arterial and venous ends of the organ, the perfusion may also be stopped after completion of the explantation of that organ. Next, the organ, for instance the liver 3.3, is positioned in the container 14.3 (see FIG. 3). The arterial and venous supply ends 65.3, 65.4 of the supply conduits 67.3, 97 are connected to respective afferent blood vessels of the organ 3.3. The valves 69.1, 69.2, 69.3, 69.5 are set for leading perfusion liquid flow into the branch 67.3 only and perfusion of the liver 3.3 in the container 14.3 is started. Subsequently, the first kidney 3.1 and the second kidney 3.2 are explanted as well an connected in a corresponding manner (FIGS. 4 and 5), each time the perfusion of the added organ is started prior to connection of the next organ to the associated supply end of the supply conduit 67. If the donor organ is a lung, the arterial supply end 65.1 or 65.2 is connected to the pulmonary artery, while the trachea of the lung is connected to a ventilator of a mechanical respirator (not shown) of the type found in anesthesia devices.

Thus, both in-donor perfusion and perfusion of the explanted organ can be achieved with the same treatment apparatus 1. A particular advantage of using the same treatment apparatus 1 is, that the composition and temperature of the perfusion liquid can easily be ensured to be the virtually same during in-donor perfusion and perfusion of the explanted organ. Thus, it is avoided that the organ 3 is subjected to a sudden change in temperature and composition of the perfusion liquid. Furthermore, the need of preparing a second perfusion circuit, as well as the risks of contamination from a second circuit, are avoided. Furthermore, although a certain minimum volume of perfusion liquid is required to avoid toxic concentrations of metabolic waste products, less perfusion liquid is required than if a second perfusion circuit is used for perfusion ex-vivo.

Because the outlet port coupling 10.5 for connection to a perfusion catheter 45 is arranged to communicate with the supply conduit 67 upstream of the container sections 35.1, 35.2 and 35.3 of the supply conduit 67, and the inlet port coupling 9.5 for connection to a return catheter 46 is arranged to communicate with the return conduit 68 downstream of the container sections 36.1, 36.2 and 36.3 of the return conduit 68, the catheters 45, 46 can be connected, perfused and disconnected independently of the presence of containers 14.1, 14.2, 14.3.

Furthermore, because a valve structure 69.1, 69.2, 69.3 and 69.5 is provided for selectively blocking or allowing liquid flow to the outlet port coupling 10.5 for connection to a perfusion catheter 45 and for selectively blocking or allowing liquid flow to or from the container sections 35.1, 35.2, 35.3, 36.1, 36.2 and 36.3 of the supply conduit 67 and the return conduit 68, the perfusion can easily be directed selectively to the catheter 45 or to one or more organs 3.1, 3.2, 3.3 in the containers 14.1, 14.2, 14.3.

Three-way valves 69.1, 69.2 and 69.5 of the valve structure are switchable between a pre-procurement position allowing liquid flow to the outlet port coupling 10.5 for connection to the perfusion catheter 45 and blocking liquid flow to the container sections 35.1, 35.2, 35.3 of the supply conduit 67 and a post-procurement position blocking liquid flow to the outlet port coupling 10.5 for connection to the perfusion catheter 45 and allowing liquid flow to the container sections 35.1, 35.2, 35.3 of the supply conduit 67. With such valves, the treatment unit 13 can easily be switched from pre-procurement perfusion of the organs 3 in the donor 4 to post procurement perfusion of organs in the container. The three-way valves 69.1 and 69.2 can also be brought in a position directing a portion of the flow to the associated container 14.1, 14.2 and the remainder of the flow to the next container or container(s) 14.2, 14.3.

The pump 6 is arranged for generating a pulsatile flow for achieving a better perfusion of the organs 3.1, 3.2, 3.3, both before and after explantation.

Figure 5:
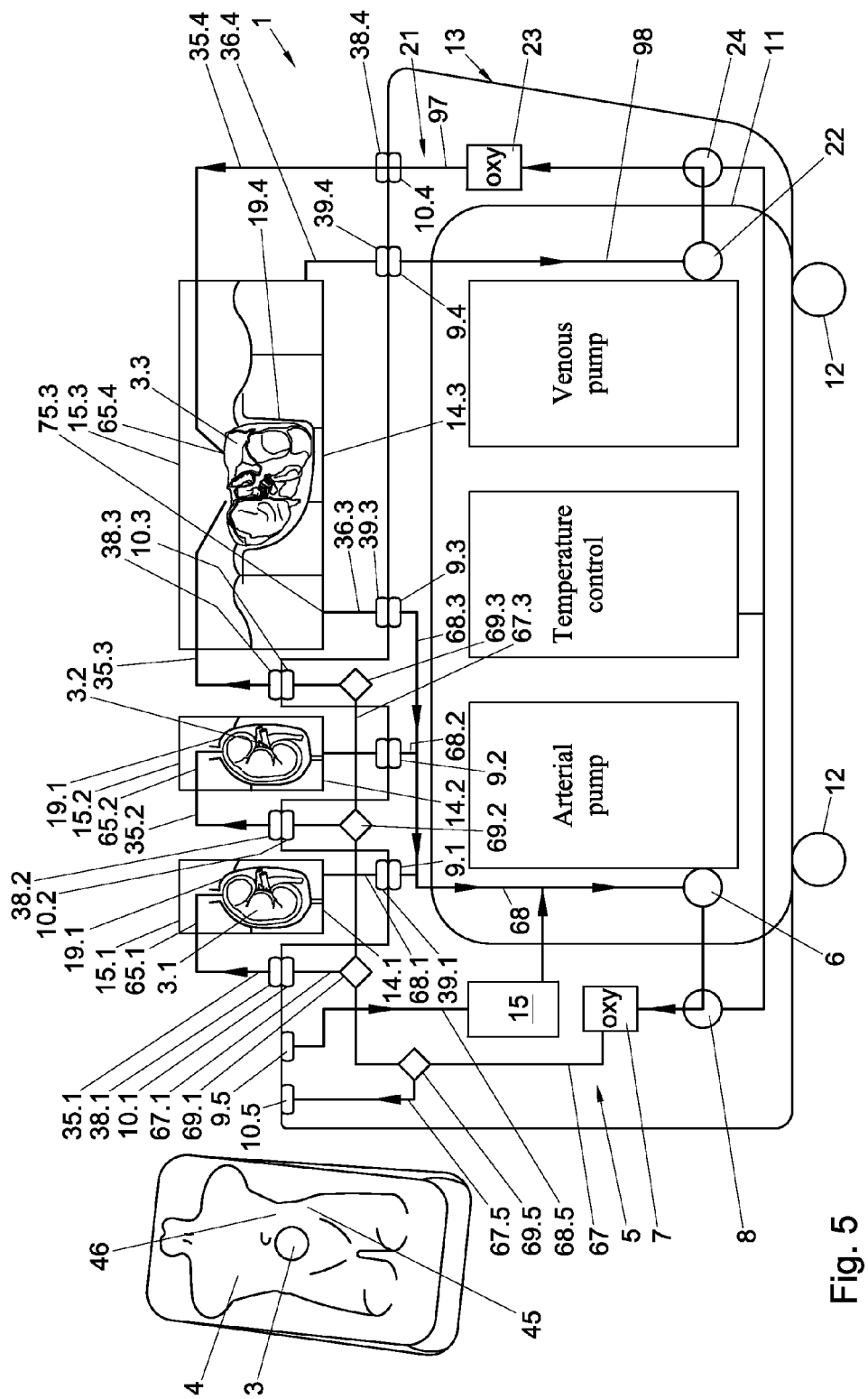

In the configuration shown in FIG. 5, the organs 3.1, 3.2, 3.3 are then cooled or cooled further by perfusing the organs 3.1, 3.2, 3.3 with a perfusion liquid circulating through the organs 3.1, 3.2, 3.3 and the perfusion liquid circuit 5 of the treatment apparatus 1. The perfusion liquid is cooled as it passes through the heat exchanger 8 of the treatment apparatus 1. If the organ 3 is not to be transported to another site, but immediately to be implanted, it is also possible to skip cooling and to rewarm the organ 3 gradually or stepwise to a temperature at which the organ's condition can be tested (e.g. by analyzing the perfusion properties and the composition of the return flow of the perfusate) or at which the organ can be implanted by heating the perfusion liquid as it passes through the heat exchanger. The treatment apparatus 1 has an adjustable thermostatic control connected to the heater 16 and the cooler 17.

The apparatus 1 has a plurality of containers 14.1, 14.2, 14.3, a plurality of supply conduits (or supply conduit branches) 67.1, 67.2, 67.3 downstream of the oxygenator 7 and the heat exchanger 8 for supplying perfusion liquid from the oxygenator 7 and the heat exchanger 8 to the organs 3.1, 3.2, 3.3 in the containers 14.1, 14.2, 14.3, and a plurality of return conduits (or return conduit branches) 68.1, 68.2, 68.3 upstream of the oxygenator 7 and the heat exchanger 8 for guiding perfusion liquid from the organs in the containers 14.1, 14.2, 14.3 to the oxygenator 7 and the heat exchanger 8. Thus, several organs explanted from the same donor can be preserved and conditioned prior to transport or implantation on the same apparatus.

After the organs 3.1, 3.2, 3.3 have been conditioned and in as far as the viability thereof has been assessed to be sufficient for implantation, the organ 3.1, 3.2 and 3.3 can be transported away if the implantation is to be carried out at a different site.

To this end, after perfusion has been stopped, the inlet and outlet port couplings 38.1, 38.2, 38.3, 38.4, 39.1, 39.2, 39.3, 39.4 of the containers 14.1, 14.2, 14.3 are uncoupled from the inlet and outlet port couplings 9.1, 9.2, 9.3, 9.4, 10.1, 10.2, 10.3, 10.4 of the treatment unit portion 13 of the apparatus 1 and the container 14.1, 14.2, 14.3 are removed from the treatment unit portion 13 of the apparatus 1, so that a situation as shown in FIGS. 6 and 7 is achieved. The containers 14.1, 14.2, 14.3 may all be removed from the treatment unit portion 13 of the apparatus 1 after the perfusion has been stopped. However, if for example the kidneys are ready for transport while the liver has to be conditioned further or if one or more of the organs is not to be transported to a different location, perfusion may be resumed for the organs that are not or not yet to be transported.

The containers are then each positioned in one of the portable transport units 2.1, 2.3 and the inlet and outlet port couplings 38.1, 38.2, 38.3, 38.4, 39.1, 39.2, 39.3, 39.4 of the containers 14.1, 14.2, 14.3 are coupled to the inlet and outlet port couplings 33.1, 33.3, 33.4, 34.1, 34.3, 34.4 of the respective one of the transport units 2.1, 2.3 as is shown in FIGS. 8 and 9.

The inlet and outlet port couplings 9.1, 9.2, 9.3, 9.4 of the treatment unit 13 are positioned in a configuration identical to the configuration of the corresponding inlet and outlet port couplings 33.1, 33.3, 33.4, 34.1, 34.3, 34.4 of the transport units 2.1, 2.3. The port couplings 38.1, 38.3, 38.4, 39.1, 39.3, 39.4 of the containers 14.1, 14.3 are in a mutually fixed configuration for each container, each of these configurations matching the associated configuration of the port couplings of the treatment unit or, respectively, the associated type of transport unit. Thus, the containers 14.1 and 14.3 can easily and quickly be connected and disconnected to and from both an associated position at the treatment unit and an associated type of transport unit. It is observed that such effects of these features can also be achieved in a system of which the organ treatment apparatus of which the supply conduit is not provided with an outlet port coupling for connection to a perfusion catheter, and of which the return conduit is not provided with an inlet port coupling for connection to a return catheter.

For preserving the conditioned organs 3.1, 3.3 during transport, the organs 3.1, 3.3 are perfused with a perfusion liquid circulating through the organs 3.1, 3.3 and the perfusion liquid circuit 25.1, 25.3 of the transport units 2.1, 2.3 as the organs 3.1, 3.3 are transported in the transport units 2.1, 2.3. Energy is supplied from the battery of the transport unit to the drive 29.1, 29.3 of the pump 28.1, 28.3 of the transport unit 2.1, 2.3. The pumps 28.1, 28.3 drives the circulation of the perfusion liquid through the organs 3.1, 3.3 and the perfusion liquid circuit 25.1, 25.3 of the transport units 2.1, 2.3. The transport units may be equipped with electric power supply connections to allow power supply and/or recharging of the battery from outside during transport. The connection may for instance be connected to the electric power supply of a vehicle in which the transport unit is transported.

Figure 10:
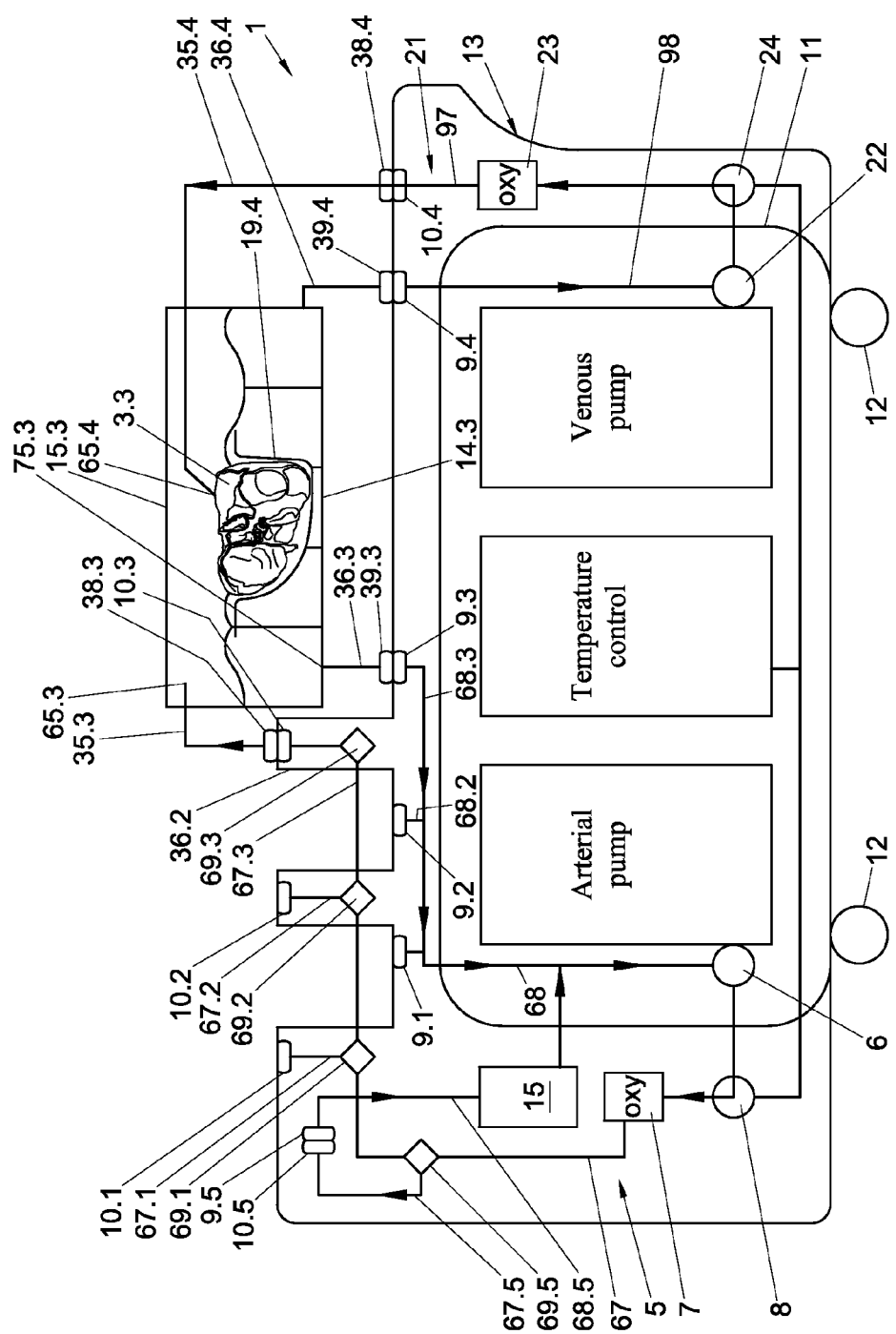
Figure 11:
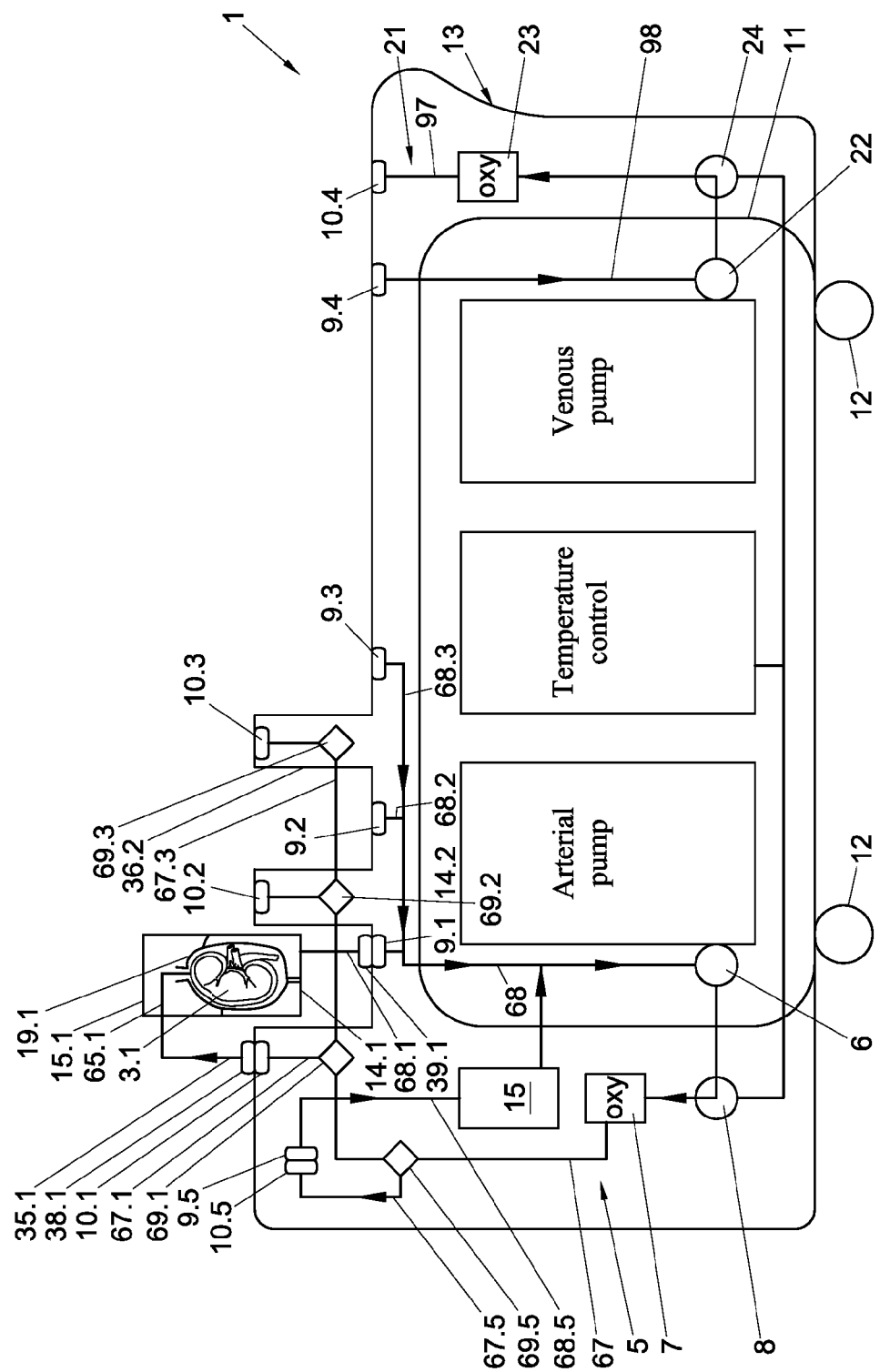

When the transported organs 3.1, 3.3 arrives at the site of the patient in which the organ is to be implanted, for instance another transplantation center, the container can be removed from the transport units 2.1, 2.3 and placed in separate treatment units 13 of the same type as the one shown in FIGS. 1-5 at different implantation sites for conditioning of the organs in preparation of implantation (see FIGS. 10 and 11). The organ is preferably oxygenated by supplying oxygen to the perfusion liquid as it flows through the oxygenator. If the organ is a lung, oxygenation is preferably carried out via air supplied to the lung by a mechanical ventilator of a type found in anesthesia devices. As the organ is treated at the treatment apparatus 1, it may be rewarmed to room or body temperature and measurements can be performed on the basis of which the viability of the organ 3 can be estimated. Since the organs 3.1, 3.3 can thus be conditioned for preservation, preserved, transported and conditioned and tested briefly before implantation in the same containers, the organs can be handled very quickly and with little risk of damage and contamination.

Figure 12:
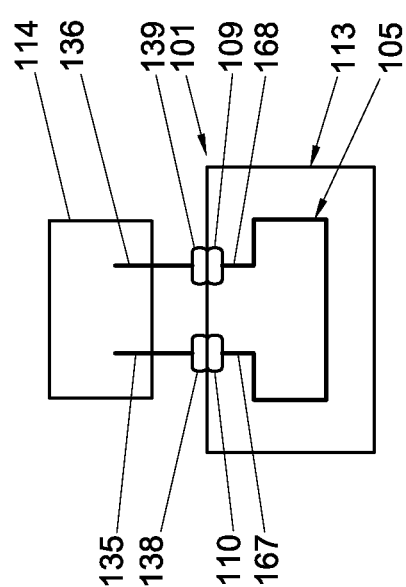

Within the framework of the invention as defined by the claims, many other embodiments than the example described above are conceivable. For instance, as illustrated by FIG. 12, the inlet port coupling 138 of the container section 135 of the supply conduit 167 may be or be arranged to be releasably coupled to the outlet port coupling 110 of the treatment unit 113 for connection to a perfusion catheter, and the outlet port coupling 139 of the container section 136 of the return conduit 168 may be or be arranged to be releasably coupled to the inlet port coupling 109 of the treatment unit 113 for connection to a return catheter. After the catheters have been uncoupled from the inlet and outlet port couplings 109, 110 of the treatment unit 113, the container 113 can be coupled to the same inlet and outlet port couplings 109, 110 of the treatment unit 113. Accordingly, no additional inlet and outlet port couplings for coupling the catheters to the perfusion circuit 105 are needed.

Figure 13:
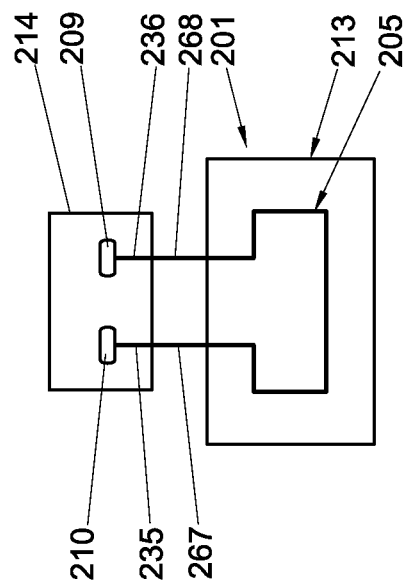
FIGS. 12 and 13 are schematic representations of alternative examples of a treatment apparatus according to the invention.

Alternatively, as illustrated by FIG. 13, the container section 235 of the supply conduit 267 may be provided with the outlet port coupling 210 for connection to a perfusion catheter, and the container section 236 of the return conduit 268 may be provided with the inlet port coupling 209 for connection to a return catheter. In this embodiments, after uncoupling of the perfusion catheter and the return catheter, coupling to conduits for supplying perfusion liquid to the organ and for draining perfusion liquid from the container may be coupled to the inlet and outlet port couplings 209, 210 of the container from which the catheters have been uncoupled. Such conduits for supplying perfusion liquid to the organ may for instance be integrated in a cartridge for holding and submerging the organ as is described in applicant's international patent application WO 2009/041806.

The invention claimed is:

1. A method for conditioning and preserving a transplantable organ, comprising:
   prior to explantation from a deceased donor body having a vascular system, perfusing the organ in the deceased donor body via catheters inserted in the donor body, the vascular system and a perfusion liquid flow path through an organ treatment apparatus, said flow path including supply and return conduits, with liquid circulating through the organ, the vascular system, the catheters and said perfusion liquid flow path through said organ treatment apparatus;
   explanting the organ;
   positioning the explanted organ in a container of said organ treatment apparatus;
   connecting said supply conduit of said treatment apparatus to a blood vessel of said organ; and
   perfusing said organ in said container with liquid circulating through said organ and said perfusion flow path through said organ treatment apparatus.

2. A method according to claim 1, further comprising:
   uncoupling inlet and outlet port couplings of the container from inlet and outlet port couplings of the perfusion flow path through the organ treatment apparatus;
   removing the container from the organ treatment apparatus;
   positioning the container in a portable transport unit and coupling the inlet and outlet port couplings of the container to inlet and outlet port couplings of a perfusion flow path through the transport unit, the transport unit being separate from the organ treatment apparatus; and
   perfusing the organ with a perfusion liquid circulating through the organ and the perfusion liquid flow path through the transport unit.

3. A method according to claim 2, further comprising:
   uncoupling inlet and outlet port couplings of the container from the inlet and outlet port couplings of the perfusion flow path through the portable transport unit;
   removing the container from the portable transport unit;
   positioning the container in a second organ treatment apparatus and coupling the inlet and outlet port couplings of the container to inlet and outlet port couplings of a perfusion flow path through the second organ treatment apparatus, the second organ treatment apparatus being separate from the transport unit;
   perfusing the organ in the container with liquid circulating through the organ and the perfusion flow path through the second organ treatment apparatus.

4. A method according to claim 1, wherein a plurality of organs is explanted, at least some of said organs are each positioned in one of a plurality of containers, and perfusing said organs in said containers with liquid circulating through said organs and said perfusion flow path through a single treatment unit of said apparatus.

5. A method according to claim 4, wherein at least some of said organs are subsequently each transported in a separate portable transport unit.

6. A method for conditioning and preserving a transplantable organ, comprising:
   providing an organ treatment apparatus for conditioning and preserving an organ of a donor, the organ treatment apparatus comprising:
      a container for holding an organ; and
      a perfusion liquid flow path extending through:
         a pump;
         an oxygenator;
         a heat exchanger for at least cooling or heating liquid in the perfusion liquid circuit passing the heat exchanger;
         a supply conduit downstream of the oxygenator and the heat exchanger for supplying perfusion liquid from the oxygenator and the heat exchanger to an organ in the container, and;
         a return conduit upstream of the oxygenator and the heat exchanger for guiding perfusion liquid from the organ inside the container to the oxygenator and the heat exchanger,
   wherein the supply conduit has a branch which is provided with an outlet port coupling connected to a perfusion catheter;
   wherein the return conduit has a branch which is provided with an inlet port coupling connected to a return catheter; and
   wherein the perfusion liquid flow path further extends through a valve structure for selectively blocking or allowing liquid flow to the outlet port coupling connected to one of the perfusion catheters and for selectively blocking or allowing liquid flow to the container, the valve structure being set for allowing liquid flow to the outlet port coupling connected to said one of the perfusion catheters and for blocking liquid flow to the container;
   prior to explantation from a deceased donor body having a vascular system, perfusing the organ in the deceased donor body via catheters inserted in the donor body, the vascular system and said perfusion liquid flow path through said organ treatment apparatus with liquid circulating through said organ, said catheters and said perfusion liquid flow path;
   explanting said organ;
   positioning said explanted organ in said container of said organ treatment apparatus;
   connecting said supply conduit of said organ treatment apparatus to a blood vessel of said organ;
   operating the valve structure for blocking liquid flow to the outlet port coupling connected to said one of said perfusion catheters and for allowing liquid flow to said container; and
   perfusing said organ in said container with liquid circulating through said organ and said perfusion flow path.

* * * * *